United States Patent [19]

Bauer et al.

[11] Patent Number: 5,098,964
[45] Date of Patent: Mar. 24, 1992

[54] PROCESS FOR PREPARING LOW-CHLORINE EPOXY RESINS

[75] Inventors: Ronald S. Bauer; Kailash C. B. Dangayach, both of Houston, Tex.

[73] Assignee: Shell Oil Company, Houston, Tex.

[21] Appl. No.: 648,780

[22] Filed: Jan. 31, 1991

[51] Int. Cl.$^5$ .................. C08G 59/06; C08G 59/08
[52] U.S. Cl. .................. 525/507; 528/90; 528/93; 528/95; 528/98
[58] Field of Search .............. 525/507, 385, 534; 528/89, 90, 93, 95, 98; 549/514, 515, 516, 517

[56] References Cited

U.S. PATENT DOCUMENTS

| | | | |
|---|---|---|---|
| 3,013,087 | 12/1961 | Schwarzer | 568/270 |
| 4,153,621 | 5/1979 | Hartmann | 549/560 |
| 4,661,644 | 4/1987 | Silvis | 568/723 |
| 4,722,983 | 2/1988 | Monnier | 525/507 |
| 4,778,863 | 10/1988 | Wang | 525/507 |
| 4,785,061 | 11/1988 | Wang | 525/507 |

*Primary Examiner*—John Kight, III
*Assistant Examiner*—Shelley A. Wright

[57] ABSTRACT

A process is disclosed for preparing a low-chlorine tetrafunctional epoxy resin which employs crystallization of the epoxy resin from solution in a finishing step of the preparation process. The process involves (a) contacting, in a basic reaction medium, epichlorohydrin and a tetraphenol of ethane to produce a reaction product mixture containing a polyglycidyl ether of the tetraphenol of ethane; (b) dissolving the polyglycidyl ether in an organic solvent and, optionally, contacting the polyglycidyl ether with a dehydrochlorination agent; and (c) reducing the temperature of the organic solvent so as to effect crystallization of a low-chlorine fraction of the polyglycidyl ether.

24 Claims, No Drawings

PROCESS FOR PREPARING LOW-CHLORINE EPOXY RESINS

BACKGROUND OF THE INVENTION

This invention relates to the production of epoxy resins. In one aspect, the invention relates to the production of low-chlorine tetrafunctional epoxy resins suitable for electronics applications.

Epoxy resins are used in the electronics inductry for encapsulating semiconductors and other sensitive electronic parts. Encapsulation formulations typically contain an epoxy resin, a curing agent and a filler material such as silica. In the encapsulation process, the electronic part is cast with a molten encapsulation formulation which is then subjected to conditions effective to cure the epoxy resin. The resulting cured resin provides physical integrity and environmental protection for the encapsulated part.

The epoxy resin used in encapsulation formulations must meet a demanding set of criteria, including high glass transition temperature and low chlorine content. Tetrafunctional epoxy resins, such as the reaction products of epichlorohydrin and tetraphenols of ethane, for example, have high Tg and are useful in encapsulation, but these resins typically have residual chlorine levels in excess of 1500 ppm. This residual chlorine can, particularly at the high-temperature conditions which exist in current high-performance electronic systems, corrode metal parts of the underlying electronic component and will cause eventual failure of the part.

It is therefore an object of the invention to provide a process for preparing epoxy resins. In one aspect, it is an object of the invention to prepare low-chlorine tetrafunctional epoxy resins suitable for high-performance electronics applications.

BRIEF SUMMARY OF THE INVENTION

According to the invention, a process is provided for preparing a tetra(glycidyloxyphenyl)ethane, the process comprising (a) contacting, in a reaction mixture comprising a basic condensation catalyst, epichlorohydrin and a tetraphenol which can be described by the formula

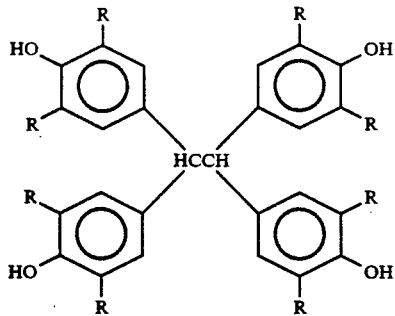

in which each R is selected independently from hydrogen, $C_{1-5}$ alkyl and halide, to produce a reaction product mixture comprising unreacted epichlorohydrin, by-product salt and a polyglycidyl ether of the tetraphenol; (b) removing unreacted epichlorohydrin and by-product salt; (c) dissolving the crude polyglycidyl ether in an organic solvent at a temperature of at least about 60° C.; (d) reducing the temperature of the solution to effect crystallization of a relatively low-chlorine fraction of the polyglycidyl ether; and (e) recovering the crystallized polyglycidyl ether. Crystallization of the tetrafunctional epoxy resin directly from the solvent has been found to produce a resin significantly lower in chlorine content than that recovered by conventional distillation of the solvent from the resin solution.

DETAILED DESCRIPTION OF THE INVENTION

The invention process involves preparation of a low-chlorine poly(glycidyloxyphenyl)ethane (hereinafter, "polyglycidyl epoxy resin") by crystallization of the polyglycidyl epoxy resin from solution in a finishing step of the process. The polyglycidyl epoxy resin is composed of a mixture of glycidated products the major portion of which is the tetraglycidyl species which can be described by the general formula

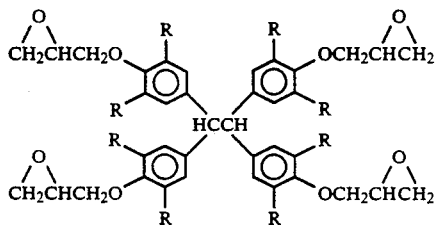

in which each R is selected independently from hydrogen, $C_{1-5}$ alkyl, preferably methyl and ethyl, and halide, preferably chloride and bromide. Such polyglycidyl epoxy resins include, for example, 1,1,2,2-tetra(4-glycidyloxyphenyl)ethane, 1,1,2,2-tetra(4-glycidyloxy-3-methylphenyl)ethane, 1,1,2,2-tetra(4-glycidyloxy-3-methyl-5-bromophenyl)ethane, 1,1,2,2-tetra(4-glycidyloxy-3,5-diethylphenyl)ethane, 1,1,2,2-tetra(4-glycidyloxy-3,5-dimethyl-2,4-bromophenyl)ethane, and the like. For currently-contemplated electronics applications, the preferred polyglycidyl epoxy resins are those in which each R is selected independently from hydrogen and methyl, such as 1,1,2,2-tetra(4-glycidyloxyphenyl)ethane and 1,1,2,2-tetra(4-glycidyloxy-3,5-dimethylphenyl)ethane, for example.

Such polyfunctional epoxy resins are generally prepared in a two-step process involving the base-catalyzed condensation reaction of a tetraphenol with a haloalkylene oxide such as epichlorohydrin, followed by a dehydrohalogenation step in which easily-hydrolyzable chloride is removed from the epoxy-functional condensation product of the first step. The condensation reaction is carried out in a reaction mixture containing a substantial excess of the epichlorohydrin and an optional organic solvent at a temperature within the range of about 60° to about 110° C. over a period within the range of about 1 to about 5 hours. The epichlorohydrin is typically present in the reaction mixture in a molar ratio with respect to phenolic hydroxyls within the range of about 2:1 to about 20:1, preferably about 4:1 to about 12:1. The preferred basic condensation catalyst is an alkali metal hydroxide such as sodium hydroxide, potassium hydroxide or lithium hydroxide, for example. The base is usually added to the reaction mixture as an aqueous solution in a concentration of about 20 to about 60, preferably about 30 to about 50, percent by weight. The base is generally employed in an amount of about 0.8 to about 1.4 moles per mole of phenolic hydroxyl and is added in increments during the course of the condensation reaction.

The condensation reaction can be carried out in an organic solvent such as a ketone, alcohol, glycol ether, polar aprotic liquid, aromatic hydrocarbon or aliphatic hydrocarbon, including such specific examples as methyl ethyl ketone, methyl isobutyl ketone, methanol, isopropyl alcohol, dimethyl sulfoxide, dimethylformamide, and the like.

The condensation reaction product mixture includes the polyglycidyl epoxy resin, excess epichlorohydrin, excess base and by-product alkali metal chloride. The reaction product mixture is filtered or siphoned for removal of solids and excess base and is distilled for removal of volatiles such as the excess epichlorohydrin and any organic solvent.

The remaining crude polyglycidyl epoxy resin contains a high level of residual chlorine which must be reduced for utility of the resin in electrical applications. The crude resin is treated by the invention finishing method for recovery of a low-chlorine fraction of the polyglycidyl ether, optionally via a dehydrohalogenation process step. In the latter option, the crude resin is treated for removal of at least a portion of easily-hydrolyzable chloride ions by contact, in an organic solvent, with a dehydrohalogenation agent such as an aqueous alkali metal hydroxide or aqueous alkali metal alkoxide, for example. Specific dehydrochlorination agents include aqueous sodium hydroxide, potassium hydroxide and potassium tert-butoxide, for example. Suitable organic solvents include ketones, alcohols, aliphatic hydrocarbons, and aromatic hydrocarbons, with ketones such as methyl ethyl ketone and methyl isobutyl ketone currently preferred because of the effectiveness of these solvents both for dehydrochlorination and as a crystallization medium for the polyfunctional epoxy resin. A co-solvent such as an alcohol can be employed so long as it does not significantly interfere with subsequent crystallization of the polyglycidyl ether. The currently-preferred co-solvent is isopropyl alcohol.

The dehydrochlorination step is typically carried out at an elevated temperature within the range of about 60° to about 110° C., preferably about 80° to about 100° C., over a time of at least about 0.5 hour, preferably about 1 to about 4 hours. The dehydrochlorination product mixture includes the polyglycidyl epoxy resin in solution and an aqueous phase containing excess dehydrochlorination agent and by-product salt, which are removed by suitable means such as filtration or siphoning.

Alternatively, the crude polyglycidyl ether of the tetraphenol can be directly treated by the invention finishing process for recovery of a low-chlorine fraction of the polyglycidyl ether. The crude polyglycidyl ether from the condensation reaction is dissolved in an organic solvent at a temperature above about 60° C. In either embodiment (with or without the use of a dehydrohalogenation step), the temperature of the solution of poly(glycidyloxyphenyl)ethane is then reduced to a level at which solid resin crystallizes from the solution. The optimum temperature of crystallization will vary depending upon the resin, but the tetrafunctional resin will generally begin to crystallize at about 60° C., with higher yields achievable within the range of about 50° C. to about 25° C. The solution can simply be permitted to cool to room temperature, or more rapid cooling can be effected by refrigeration, heat exchange, etc. Highest yields of a low-chlorine fraction can be achieved by permitting the solution to cool slowly to about 40° C., stirring at this temperature for 2-5 hours, and then stirring at about 25° C. for an additional 4-8 hours. It may be desirable to seed the solution with a crystalline material such as previously-recovered polyglycidyl epoxy resin. The crystalline epoxy resin can be recovered by filtration or centrifugation. The recovered crystalline polyglycidyl epoxy resin typically has a chlorine content below about 500 ppm, optimally below about 300 ppm, and can be recovered at yields as high as about 40–60 percent. The remaining solution can be treated by conventional means, such as distillation under vacuum, for recovery of polyglycidyl epoxy resin for use in applications with less demanding requirements for low chlorine content.

EXAMPLE 1

An experiment was performed to compare the chlorine levels of polyglycidyl ethers of 1,1,2,2-tetrakis(4-hydroxy-3,5-dimethylphenyl)ethane prepared using conventional evaporation recovery with a glycidyl ether prepared using the invention process.

The precursor phenol was prepared as follows. Into a 5000-ml, 4-neck flask fitted with a mechanical stirrer, condenser, thermocouple and addition funnel were charged 158.4 g of 40% w aqueous glyoxal, 2000 g 2,6-xylenol, 40 ml hydrochloric acid and 750 ml methanol. The reaction mixture was stirred and heated at reflux for about 36 hours. On cooling, a solid product crystallized from the reaction mixture. The solid was recovered by filtration and was washed with methanol until the filtrate was clear and the product appeared white. On drying overnight at 60° C. in a vacuum oven, 386 g (yield 69%) of product were obtained.

The polyglycidyl ether of the tetraphenol was prepared as follows. Into a 5000-ml 4-neck flask equipped with a stirrer, thermocouple, condenser, nitrogen inlet, heating mantle and addition funnel were charged the following:

| | |
|---|---|
| tetraphenol (g) | 255 |
| epichlorohydrin (g) | 1851.5 |
| isopropyl alcohol (g) | 1080 |
| water (g) | 312.5 |

The reaction mixture was heated to 70° C., and 20% aqueous NaOH was added in three separate increments of 190 g, 160 g and 90 g, each increment added over a period of one hour. After the final addition was complete, the reaction mixture was held at 70° C. for 30 minutes, and brine was removed by siphoning. The reaction mixture was then rotovapped at 150° C. to remove excess epichlorohydrin and solvent.

The dry product was dehydrohalogenated by dissolving in methyl isobutyl ketone and adding 1500 ml of 5% aqueous NaOH in a 5000 ml 4-neck flask equipped with stirrer, thermocouple, condenser, nitrogen inlet and heating mantle. The reaction mixture was heated to reflux temperature (about 92° C.) and held for 2 hours. The brine was removed and the remaining reaction mixture was water-washed with hot tap water four times, with removal of the aqueous layer each time.

The reaction mixture was divided into two batches. The comparison batch was rotovapped to dryness at 150° C. The invention batch was allowed to cool to room temperature overnight, and crystallized product was recovered, filtered, washed with hexane and dried in a vacuum oven at 50° C. overnight. The weight per epoxide (WPE) and total chlorine content of each sample were determined. Results are shown in Table 1.

TABLE 1

| | WPE | Total Cl(ppm) | Yield(%) |
|---|---|---|---|
| Comparison product | 205 | 1403 | 92 |
| Crystallized product | 195 | 278 | 57 |

As can be seen in Table 1, the product obtained by crystallization has a substantially lower chlorine content than that obtained by solvent distillation, without significant reduction of WPE.

We claim:

1. A process for preparing a tetra(glycidyloxyphenyl)ethane comprising the steps of:
   (a) contacting, in a reaction mixture at a temperature within the range of about 60° C. to about 110° C., epichlorohydrin and a tetraphenolic compound which can be represented by the formula

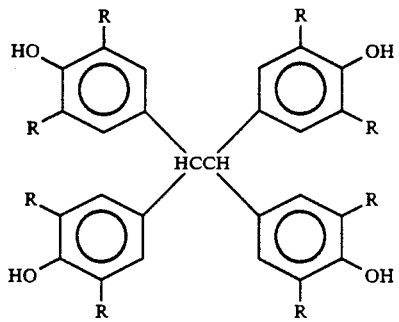

in which each R is independently selected from hydrogen, $C_{1-5}$ alkyl and halide, in the presence of a basic condensation catalyst to produce a reaction product mixture comprising unreacted epichlorohydrin, by-product salt and a polyglycidyl ether of the tetraphenolic compound;
   (b) removing unreacted epichlorohydrin and salt from said reaction product mixture;
   (c) dissolving the remaining crude polyglycidyl ether in an organic solvent at a temperature of at least about 60° C.;
   (d) reducing the temperature of said solution to effect crystallization of a relatively low-chlorine fraction of said polyglycidyl ether; and
   (e) recovering a crystallized polyglycidyl ether.

2. The process of claim 1 in which the organic solvent of step (c) is selected from ketones, alcohols, aliphatic hydrocarbons and aromatic hydrocarbons.

3. The process of claim 1 in which the organic solvent for step (c) comprises a ketone.

4. The process of claim 1 in which the organic solvent comprises at least one of methyl ethyl ketone and methyl isobutyl ketone.

5. The process of claim 1 in which the R moiety of the tetraphenolic compound is selected from hydrogen and methyl.

6. The process of claim 3 in which the tetraphenolic compound is 1,1,2,2-tetra(4-hydroxy-3,5-dimethylphenyl)ethane.

7. The process of claim 1 in which the tetraglycidyl ether comprises 1,1,2,2-tetra(4-glycidyloxy-3,5-dimethylphenyl)ethane.

8. The process of claim 3 in which the temperature reduction of step (d) is accompanied by stirring of the solution.

9. The process of claim 3 in which the crystallized polyglycidyl ether has a total chlorine content less than about 500 ppm.

10. A process for preparing a tetra(glycidyloxyphenyl)ethane comprising:
    (a) contacting, in a reaction mixture at a temperature within the range of about 60° C. to about 110° C., epichlorohydrin and a tetraphenolic compound which can be represented by the formula

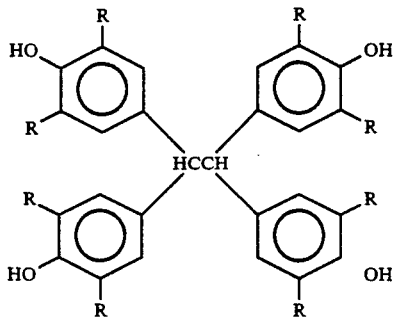

in which each R is independently selected from hydrogen, $C_{1-5}$ alkyl and halide, in the presence of a basic condensation catalyst to produce a reaction product mixture comprising unreacted epichlorohydrin, by-product salt and a polyglycidyl ether of the tetraphenolic compound;
    (b) removing unreacted epichlorohydrin and salt from said reaction product mixture;
    (c) dissolving the remaining crude polyglycidyl ether in an organic solvent and contacting said crude polyglycidyl ether with a dehydrohalogenation agent for a time of at least about 0.5 hour to produce a dehydrohalogenation product mixture comprising the polyglycidyl ether in solution;
    (d) reducing the temperature of said solution to effect crystallization of said polyglycidyl ether; and
    (e) recovering a crystallized polyglycidyl ether.

11. The process of claim 10 in which the organic solvent of step (c) is selected from ketones, alcohols and aromatic hydrocarbons.

12. The process of claim 10 in which the organic solvent of step (c) comprises a ketone.

13. The process of claim 10 in which the organic solvent comprises at least one of methyl ethyl ketone and methyl isobutyl ketone.

14. The process of claim 10 in which the R moiety of the tetraphenolic compound is selected from hydrogen and methyl.

15. The process of claim 12 in which the tetraphenolic compound is 1,1,2,2-tetrakis(4-hydroxy-3,5-dimethylphenyl)ethane.

16. The process of claim 10 in which the tetraglycidyl ether comprises 1,1,2,2-tetrakis(4-glycidyloxy-3,5-dimethylphenyl)ethane.

17. The process of claim 12 in which the dehydrochlorination agent is sodium hydroxide.

18. The process of claim 17 in which the temperature reduction of step (d) is accompanied by stirring of the solution.

19. A process for preparing a tetra(glycidyloxyphenyl)ethane having a chlorine content less than about 500 ppm, the process comprising the steps of:
    (a) dissolving a crude tetra(glycidyloxyphenyl)ethane having a chlorine content greater than about 1000 ppm in an organic solvent and contacting said crude tetra(glycidyloxyphenyl)ethane at an elevated temperature with a base for a time of at least about 0.5 hour to produce a dehydrochlorination product mixture comprising the tetra(glycidyloxyphenyl)ethane in solution;

(b) reducing the temperature of said solution to effect solidification of said tetra(glycidyloxyphenyl)ethane in a crystalline form having a chlorine content less than about 500 ppm.

20. The process of claim 19 in which the base of step (a) is sodium hydroxide and the contacting is carried out at a temperature of at least about 60° C.

21. The process of claim 20 in which the organic solvent comprises a ketone.

22. The process of claim 19 in which the organic solvent comprises at least one of methyl ethyl ketone and methyl isobutyl ketone.

23. The process of claim 21 in which the tetra(glycidyloxyphenyl)ethane is 1,1,2,2-tetrakis(glycidyloxy-3,5-dimethylphenyl)ethane.

24. The process of claim 19 in which the reduction in temperature of the solution is accompanied by stirring of the solution.

* * * * *